United States Patent [19]

Bedding

[11] 4,178,366

[45] Dec. 11, 1979

[54] NEMATODE LARVAE AS BIOLOGICAL INSECTICIDES

[75] Inventor: Robin A. Bedding, Taroona, Australia

[73] Assignee: Commonwealth Scientific and Industrial Research Organization, Australia

[21] Appl. No.: 909,404

[22] Filed: Feb. 21, 1978

Related U.S. Application Data

[63] Continuation of Ser. No. 715,590, Aug. 18, 1976, abandoned.

[30] Foreign Application Priority Data

Aug. 26, 1975 [AU] Australia ................. 2930/75

[51] Int. Cl.$^2$ ............................................. A01N 15/00
[52] U.S. Cl. ....................................... 424/93; 424/366
[58] Field of Search ................... 424/93, 167, 366

[56] References Cited

U.S. PATENT DOCUMENTS 3,271,243  9/1966  Cords et al. ........................ 424/93

OTHER PUBLICATIONS

Chemical Abstracts, vol. 67 (1967), p.20958e.
Blachere et al., Abstract of French Pat. No. 2,202,159 (3-1974).

*Primary Examiner*—V. D. Turner
*Attorney, Agent, or Firm*—Sughrue, Rothwell, Mion, Zinn & Macpeak

[57] ABSTRACT

A formulation for use in the biological control of insects, particularly insect pests, comprises an oil suspension of the infective stage of nematodes such as *Neoaplectana carpocapsae* parasitic to the larvae of those insects. The formulation may be distributed in the form of droplets or films of oil containing this infective stage of the nematodes. Also disclosed is a method and assemblage for rearing nematodes.

20 Claims, No Drawings

NEMATODE LARVAE AS BIOLOGICAL INSECTICIDES

This is a continuation of application Ser. No. 715,590, filed Aug. 18, 1976, now abandoned.

This invention relates to the use of nematodes for biological control of insect pests.

The infective larvae of *Neoaplectana carpocapsae* have been observed to destroy a wide range of insect pests under laboratory conditions. This ability is accounted for by the nematode's own pathogenicity towards the insects, and by its association with the entomogenous bacteria, *Achromobacter nematophilus*, which is usually to be found in the intestinal lumen of infective species. Following ingestion by an insect, the nematode will usually penetrate the gut wall to enter the haemocoel and release *A. nematophilus*, which multiply and lead to the death of the host by septicaemia. Additionally, there will often be reproduction of the nematodes in the dead host and hence generation of further infective organisms.

In the light of the above, many proposals for the use of infective larvae of *N. carpocapsae* in the biocontrol of insects, have been published since the nematodes were first investigated. A major obstacle to the implementation of such proposals has, however, been the susceptibility of nematodes to desiccation. Their apparent need for free water has led to suggestions that they be applied via aqueous media to bark or foliage on which the insect pests feed, but only limited effectiveness has been achieved with this technique under field conditions because of evaporation of the water before the nematodes locate and become established in the host. In order to reduce the rate of evaporation, it has been advocated that aqueous formulations should include, for example wax evaporation-retardant water thickeners, and gelling agents or surfactants. Unfortunately there is little evidence that such formulations so extend the lifetime of nematodes in the field after application that they can be regarded as offering an effective and practical method of insect control.

The present invention is based upon the surprising discovery that infective nematodes will remain active for substantial periods of time in the absence of free water, provided their body moisture, oxygen supply and mobility can be maintained. In accordance with the present invention, this is achieved by use of oil instead of water as a medium in which to store or disperse the nematodes.

The present invention therefore provides an insecticidal formulation for use in the biological control of insects, comprising an oil suspension of the infective stage of nematodes parasitic to the larvae of said insects.

Also, the present invention comprises a method for the biological control of insects having larval stages that feed upon the bark or foliage of plants, said method comprising distributing upon the plants, droplets or films of oil containing the infective stage of nematodes parasitic to said insect larvae.

Many natural and synthetic oils possess appropriate oxygen permeability (i.e. high, relative to water), ability to reduce loss of body moisture, and mobility, to render them useful for this invention, but some care is obviously necessary to avoid materials which although satisfactory in terms of physical properties, are toxic to the parasites. Optimum physical properties will vary according to factors such as the mode of application of the oil suspension and the conditions prevailing at the time of application. The man skilled in the art should have no difficulty, however, in devising formulations to meet his requirements from the teachings herein. For most purposes a light mineral oil is recommended, and preferably a paraffinic oil containing no additives; we have found mineral oils with S.A.E. viscosity ratings in the range of about 50–250 to be satisfactory. One commercial example is DENTAX 140 oil produced by the Shell Company, another is TALPA 60, also produced by the Shell Company.

A preferred feature of formulations according to this invention is the addition of waxes and wax-like materials to the oil, to assist in reducing moisture loss from the nematodes. The beneficial effect of the wax is believed to derive from its tendency to migrate to the exterior of the oil droplet and form a coating which is substantially impermeable to water but not to oxygen. The wax is selected so as to have a melting point above the ambient temperature likely to be encountered during storage or in the field, but preferably it should be possible to mix it with the oil while molten in order to facilitate dispersion. Paraffin waxes with melting points of the order of 115°–145° F. are suitable when included in amounts from about 5 to 15% (by weight of oil). Although nematode survival (after spraying onto plants) is favoured by wax concentrations at the upper end of this range, a better kill is achieved with compositions containing less wax, about 6–8%, appears to be optimum; the latter compositions are also easier to spray. Although generally inferior to paraffin wax, acceptable alternatives include vaseline, petroleum jelly, wool wax, wool grease, microcrystalline wax and match wax.

Gelatin in small amounts can be of real benefit for promoting emulsification of water into the suspension, and a preferred formulation includes about 5–10 parts per 100 (b.w.), of 1% gelatin in water. Marginal benefits might also accrue from the use of other additives, often lipidic or proteinaceous in nature, which act as water retainers or perhaps to enhance the attractiveness of the formulations to insect larvae. Some examples are agar, stearic acid, oleic acid, aluminium stearate, zinc stearate, yeast, lecithin, glycerine and cetyl alcohol.

Some typical effective nematode media according to this invention have compositions of the following sort:
5–15 parts 135/145 paraffin wax
95–85 parts TALPA 60 oil.

This is not to be regarded as limiting upon the scope of the invention, for example satisfactory performance is achieved when DENTAX 140 or TALPA 50 oils are used instead of TALPA 60, or 115/125 and 125/135 paraffin waxes are substituted, in part or whole, for 135/145 paraffin wax. A preferred nematode medium composition is:
5 parts 135/145 paraffin wax
95 parts TALPA 60 oil
10 parts 1% gelatin in water.

It is difficult to say with precision how much oil medium is required to sustain a given number of nematodes; good results have been achieved with as many as 500,000/ml, but generally we prefer to work with concentrations of the order of 200,000/ml.

When applied in an oil/wax formulation such as described above, the loss of moisture is so retarded that the nematodes take several hours to several days to desiccate, and even then they may be revived by moistening, as will occur upon ingestion by an insect. By contrast, nematodes subjected to the rapid drying, which is a feature of techniques employing aqueous formulations, die within a few minutes of the free water being lost.

Another discouragement to the use of nematodes as insect biocontrol agents hitherto, has arisen when attempts have been made to produce nematodes in quantity. Although small batches can be reared quite successfully in small vessels, such as petri dishes, containing growth media, when larger vessels are used the output is not found to be commensurate with the increased scale of operations. We believe this is because large uninterrupted masses of growth media are more easily contaminated by foreign bacteria, and also they are difficult structures to aerate and to harvest nematodes from. Such problems are minimized in a new method provided by the present invention. The new method comprises rearing nematodes in an assemblage of suitable sterilized growth media which is liberally provided with interconnected interstitial spaces to permit the free circulation of fluids, namely air for airation and washing liquids for harvesting.

An effective mass-rearing assemblage may be formed in a variety of ways, for example by loosely stacking animal organs or pieces of animal organs, or pieces of animal tissue, or pieces of inert material coated or impregnated with an animal tissue homogenate. (Animal in this discussion is intended to include avian). Small stacks may be self-supporting, but above a certain size, depending on the material being used and proportions of individual components, it may be necessary to provide supports in the form of spaced trays or grids made from plastic, stainless steel, wood or other inert material. Instead of trays or grids, assemblages of cellular or coiled material may be employed, for instance as layers interposed between layers of the pieces of growth media, or as a substantially continuous network impregnated with an animal tissue homogenate.

The output of a given stack will be related to the surface area of growth media it presents. Whilst a stack of pieces of animal material is relatively simple to construct and should remain coherent through repeated harvesting cycles without undergoing compaction or disintegration, it will be relatively inefficient from the point of view of surface area/volume ratio. We have found that a stack with high surface area/volume ratio and correspondingly better initial output, may be made from a material such as woodwool coated with a suitable animal tissue or soya bean homogenate. Among other materials useful for increasing the surface area of a stack are, wood shavings, straw, coke, choppings of plastic tubing, or sections of folded aluminium sheet. A very effective homogenate is obtained from the following components:

I { 3 parts chicken heart
    3 parts pig kidney
    2 parts water
    0.05% cholesterol.

There is little doubt, however, that thorough investigation of other combinations of the above, and similar materials will yield equally effective growth media for nematodes. By way of example only, some further homogenate formulations will now be described:

II { 3 parts chicken heart
     2 parts water.
III { 3 parts chicken heart
      1 part chicken liver
      2 parts water.
IV    Pig, ox or sheep kidney.
V  { 1 part soy bean
     4 parts water.
VI { 2 parts beef heart
     1 part water.

A typical sequence of operations involving stacks such as described above, would be, (i) adding inoculae of nematodes and entomogenous bacteria to a sterilized stack, which is maintained in a moist, aerated condition, (ii) after a period allowing for suitable multiplication, harvesting the nematodes by washing with sterile water, (iii) filtering the nematodes from the wash water, and, (iv) mixing the nematode filter cake with oil or oil and wax to produce compositions for storage or application.

The grease-like concentrates prepared according to this invention can be stored for several days if maintained at about 0°–10° C. in sealed containers which have been flushed with oxygen. When the nematodes are to be applied in the field, the grease after removal from storage is allowed to reach ambient temperature and then applied to the foliage of the affected plant through high pressure sprays which form a mist of the formulation in which droplets contain one or at most a few nematodes. Suitable spraying apparatus for small scale work is a paint spray gun, using compressed air at about 15 lbs. per square inch pressure.

For long term storage, it is known that high concentrations of nematodes can be kept alive suspended in water through which air is bubbled at a rate sufficient to ensure that all nematodes are subject to some degree of agitation. For example, we have found it possible to keep as many as $10^9$ nematodes alive for several weeks in 2 liters of water at 5° C., using a 2¼ liter flagon supported with the base at 45° to the horizontal and with air being introduced from an aquarium pump through a tube reaching into the lower corner. Under the same conditions, lesser concentrations have been kept alive for over a year. It is a simple matter to connect several containers in series to the same pump.

Having broadly portrayed the nature of the present invention, particular examples will now be described by way of illustration only.

EXAMPLE 1

In this particular example the nematode *Neoaplectana carpocapsae* strain Agriotos was employed. The nematodes were reared in monoxenic culture together with their symbiotic bacterium *A. nematophilus* to produce an inoculum of approximately one million individuals by small-scale batch culture. A media stack was formed from whole chicken hearts arranged in alternating layers with wood shavings and supported at intervals by wire mesh trays arranged vertically one above the other, within a sealable drum having inlets and outlets for sterile air at either end. The interior of the drum and its entire contents were then subjected to heat-sterilization by passing steam therethrough. The inoculae of bacteria and nematodes were mixed with sterile distilled water and simply poured into the sterile drum to disperse the microorganisms over the layers of media. The drum was then incubated at about 25° C. for about 3 weeks to allow infective nematodes to be produced. These nematodes migrated to the surface to the chicken hearts and onto the wood shavings from whence they could be readily harvested by flushing with sterile water. Sufficient nematodes and bacteria were, however, left within the drum to produce a second generation which were incubated and harvested in the same manner. In this way repeated harvestings could be effected as the chicken hearts and wood shavings stack does not compact, the chicken hearts merely shrinking in size but retaining their coherence and individuality.

The nematodes were separated from the wash water after harvesting by decanting surplus water and then filtering through a spinning screen, or other filter membrane such as Whatman's No. 1 filter paper, to produce a filter cake. Excess water was then removed from the filter cake by allowing it to stand for a short period and by dabbing with absorbent material. A concentrate of nematodes was then formed by vigorous mixing with about 10 times its own volume of a grease-like material produced by heating 8% Shell 140/145 paraffin wax and 92% Shell TALPA 60 in a water bath, and then allowing the mixture to cool to about 10° C.

EXAMPLE 2

A mixture of four parts chicken hearts to three parts water was homogenized for about three minutes in a household food blender. The homogenate was mixed by hand with dry, coarse grade Aspen woodwool; the wool being squeezed and teased so that each strand was discrete but well coated with an even layer of heart. The coated woodwool was then put into 2 liter Pyrex glass aspirators (giving about 320 g homogenate per aspirator); the mouth of each of these was closed with non-absorbent cotton wool bungs and the bottom inlet attached to an air filter tube prior to autoclaving for one hour. Monoxenic inoculum of about 1 million Neoaplectana was added through the mouth of each aspirator and air at 100% relative humidity was blown through the filter tube, entering the bottom of the aspirator and leaving at the top. The aspirator and contents were incubated at 23° C. for three weeks. A first harvesting (with sterile salt solution) yielded over $5 \times 10^7$ infective nematodes, and a similar yield was harvested after a further 3 weeks.

EXAMPLE 3

In laboratory tests, a nematode concentrate of the sort described in Example 1 was sprayed at a rate of about 250,000 nematodes per square meter of leaf onto gum trees carrying chrysomelid beetle larvae (*Chrysophtharta variicollis*). 34% of the larvae on 8 trees were killed within 3 days of spraying, and 95% were killed within a week. In a similar experiment 80% of adult *Chrysophtharta variicollis* were killed within a week of spraying.

Although the invention has been described with reference to a particular nematode species and a particular insect pest, the invention is not thereby limited. For example, insect pests which should be susceptible to attack by the formulations of this invention include the codling moth (*Cydia pomonella*), the southern ironbark beetle (*Dendroctonus frontalis*), larch sawfly larvae (*Pristiphora erichsonii*), colorado potato beetle (*Leptinotarsa decemlineata*), cabbage white butterfly (*Pieris rapae*), cutworms (*Persectania ewingi* and Euromessoria sp.) eucalyptus-sawflies (*Perga affinis* and Pterygophorus), the cup moth (Doratifera sp.), the autumn gum moth (*Mnesampela privata*) and the chrysomelids, *Chrysophtharta nobilitata, C. decolorata, C. aureus, Paropsisterna nucea, Paropsis lutea* and *P. charybdis*.

It is also to be understood that pest control technology is not the only field of application for the methods of quantity production of nematodes which are described herein. For instance live nematodes are very acceptable as food to many species of fish, and nematode cultures are commercially available for tropical fish enthusiasts to generate live food for their aquaria. It is envisaged that there would be a similar market for live adult nematodes produced by the method of this invention, particularly if packaged in watertight, air-permeable containers which were also suitable for refrigerated storage.

References in this specification to "parts" when describing growth media or oil media, is to be understood as meaning parts by weight.

The claims defining the invention are as follows:

1. A formulation for use in the biological control of insects, comprising mineral oil as a suspension medium containing an insecticidal amount of a larval stage of nematodes infective and parasitic to the larvae of said insects and a wax or wax-like material in an amount effective to reduce water loss from said formulation, said formulation substantially not containing any free water but retaining the body moisture of said nematodes.

2. A formulation according to claim 1 in which the oil is a light mineral oil.

3. A formulation according to claim 2 in which the oil has an S.A.E. viscosity rating in the range 50–250.

4. A formulation according to claim 1 in which the said wax is paraffin wax.

5. A formulation according to claim 4 in which the paraffin wax has a melting point in the range 115°–145° F.

6. A formulation according to claim 5 in which the paraffin wax has a melting point in the range 135°–145° F.

7. A formulation according to claim 4 in which the weight of paraffin wax is 5–15% by weight of the oil.

8. A formulation according to claim 7 in which the weight of paraffin wax is 6–8% by weight of the oil.

9. A formulation according to claim 1 in which the nematodes are *Neoaplectana carpocapsae*.

10. A formulation according to claim 1 wherein said wax or wax-like material is selected from the group consisting of paraffin wax, petroleum jelly, wool wax, wool grease, microcrystalline wax and match wax.

11. In a method for the biological control of insects using the larval stage of nematodes, the improvement to extent the duration of insecticidal activity of a larval stage of nematodes infective and parasitic to the larvae of insects which comprises using said larval stage of nematodes as an oil suspension thereof, said oil suspension comprising an oil as a suspension medium containing an insecticidal amount of the larval stage of nematodes infective and parasitic to the larvae of insects and a wax or wax-like material in an amount effective to reduce water loss from said suspension, said suspension substantially not containing any free water, but retaining the body moisture of said nematodes.

12. The method of claim 11 wherein the oil is a light mineral oil.

13. The method of claim 12 wherein the oil has an SAE viscosity rating in the range of 50–250.

14. The method of claim 11 wherein the wax is paraffin wax.

15. The method according to claim 14 in which the paraffin wax has a melting point in the range of 115°–145° F.

16. The method according to claim 15 in which the paraffin wax has a melting point in the range of 135°–145° F.

17. The method according to claim 14 wherein the weight of the paraffin wax is 5–15% by weight of the oil.

18. The method of claim 17 wherein the weight of paraffin wax is 6–8% by weight of the oil.

19. The method according to claim 11 wherein the nematodes are *Neoaplectana carpocapsae*.

20. The method of claim 11 wherein said wax or wax-like material is selected from the group consisting of paraffin wax, petroleum jelly, wool wax, wool grease, microcrystalline wax and match wax.

* * * * *